United States Patent [19]

Taylor et al.

[11] Patent Number: 4,819,622

[45] Date of Patent: Apr. 11, 1989

[54] ORTHOPEDIC CERVICAL SUPPORT COLLAR AND METHOD OF MAKING THE SAME

[76] Inventors: Natalee E. Taylor, 13201 SE. 197th, Boring, Oreg. 97009; John P. Bonica, 16323 SE. Stark, Portland, Oreg. 97233

[21] Appl. No.: 70,344

[22] Filed: Jul. 6, 1987

[51] Int. Cl.⁴ .............................................. A61H 1/02
[52] U.S. Cl. ............................... 128/75; 128/DIG. 23
[58] Field of Search ............ 128/75, 68, 69, DIG. 23, 128/165, 380, 163, 169

[56] References Cited

U.S. PATENT DOCUMENTS

| | | | |
|---|---|---|---|
| 1,297,398 | 3/1919 | Pine | 128/DIG. 23 |
| 1,964,962 | 7/1934 | Rosenblum | 128/DIG. 23 |
| 2,725,054 | 11/1955 | Harpel | 128/DIG. 23 |
| 3,320,950 | 5/1967 | McElvenny | 128/75 |
| 3,696,810 | 10/1972 | Gaylord | 128/75 |
| 3,916,884 | 11/1975 | Attenburrow | 128/75 |
| 3,921,626 | 11/1975 | Neel | 128/75 |
| 4,232,663 | 11/1980 | Newton | 128/75 |
| 4,336,807 | 6/1982 | Benckhuijsen | 128/DIG. 23 |
| 4,576,150 | 3/1986 | Auracher | 128/75 |

Primary Examiner—Edgar S. Burr
Assistant Examiner—Huong Q. Pham
Attorney, Agent, or Firm—Eugene D. Farley

[57] ABSTRACT

An orthopedic cervical support collar comprising a piece of thick, absorbent cloth material folded lengthwise to form an elongated, multi-ply pad having a length sufficient to encircle the neck and provide an overlap. Stitching through the cloth plies, or other suitable ply interengaging means, maintains the plies in a flat, pad-forming condition. Releasable fastening means such as burr type ("Velcro") fasteners are mounted on the pad in the area of the overlap for releasably fastening together the overlapped pad ends when mounting the pad collar-wise on the neck of the user.

A method of making the collar from a length of toweling or other thick, absorbent cloth material also is provided.

8 Claims, 1 Drawing Sheet

U.S. Patent      Apr. 11, 1989      4,819,622

ORTHOPEDIC CERVICAL SUPPORT COLLAR AND METHOD OF MAKING THE SAME

BACKGROUND AND GENERAL STATEMENT OF THE INVENTION

This invention relates to orthopedic cervical support collars.

Orthopedic cervical support collars are required for use by people suffering from cervical conditions such as neck injuries, strained necks, sore neck muscles, arthritic neck joints, bone spur pains, etc. They also can be used to advantage by the elderly and handicapped as well as by athletes with neck conditions, and by individuals who wish to insure against re-injuring their necks after a previous injury. Still further, they are useful in their provision of a neck support for individuals who drive automobiles great distances and as a result suffer from neck aches.

Commercially available prior art cervical support collars conventionally are manufactured from styrofoam, polyfoam or foamed rubber. Even though padded they are uncomfortable to the wearer since they do not conform in all respects to the curvature of the body and are stiff and unyielding. They also are abrasive, irritating and frustrating to wear. Additionally, they cause the wearer to become hot and sweaty, with resulting fouling of the collar, which is not adaptable for machine washing and drying.

As a consequence, users of the prior art collars are prone to discard them prematurely even though they still require the comfort, support and protection which a properly designed cervical support collar could provide.

It is the general purpose of the present invention to provide an orthopedic cervical support collar which overcomes the above described problems associated with the prior art collars.

The foregoing and other objects of the present invention are accomplished by the provision of an orthopedic cervical support collar which, broadly considered, comprises a piece of thick, absorbent cloth material such as cloth toweling, folded lengthwise to form an elongated, multi-ply pad having a length sufficient to encircle the neck and provide an overlap. Stitching through the plies, or other ply interengaging means, maintains the piece in flat, pad-forming condition. Releasable fastening means such as Velcro fasteners mounted on the pad in the area of the overlap make possible releasing and fastening together the overlapped pad ends when mounting the pad collar-wise on the neck of the wearer.

The foregoing support collar may be fashioned by folding a rectangular piece of cloth material longitudinally inwardly from each side to substantially the longitudinal center line, and then again along the longitudinal center line to form a four-ply pad. The plies then are fastened together by application of suitable interengaging means, preferably by stitching them together in a pattern predetermined to provide stiffened, supportive pad margins. "Velcro" or other suitable fasteners are mounted on the pad, in the area of the overlap, to provide adjustable release means for fastening the pad collar-wise on the user's neck.

THE DRAWINGS

DETAILED DESCRIPTION OF A PREFERRED EMBODIMENT OF THE INVENTION

Figure 2:
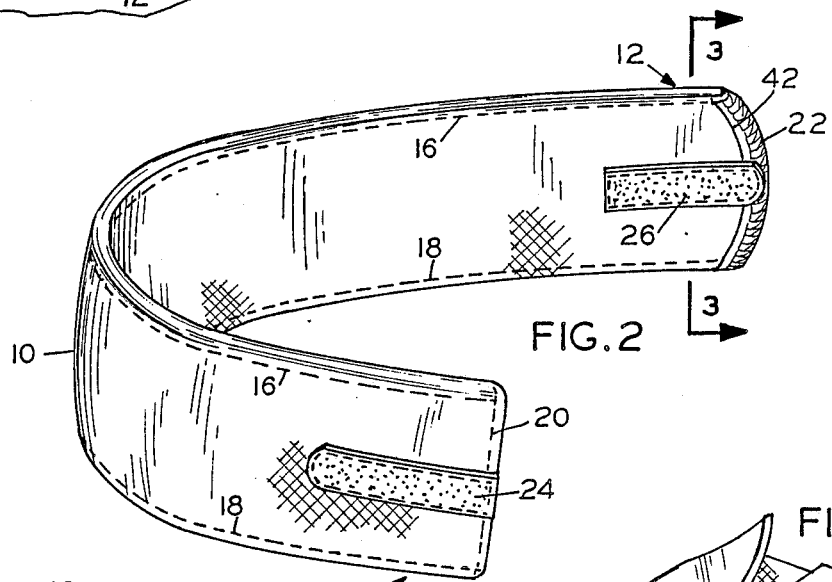
FIG. 2 is a top perspective view illustrating the appearance of the collar.

As shown in FIG. 2, the orthopedic cervical support collar of my invention comprises a pad, indicated generally at 10, formed of a plurality of longitudinally arranged plies. The pad has an overlapping end indicated at 12 and an underlapping end indicated at 14. Although the pad may be comprised of various categories of cloth material, a preferred category comprises a thick, heavy grade of commercial toweling or terry cloth.

The plies are held together by suitable interengaging means, preferably by rows of stitching which maintain the piece in a flat, pad-forming condition.

In the illustrated form of the invention there are two longitudinal stitching rows 16, 18 located a spaced distance inwardly from the longitudinal side edges of the pad. These provide stiffened, supportive longitudinal pad margins.

The underlapping end 14 of the pad is finished with a row of transverse stitching 20; the overlapping end, with a transverse row of transverse stitching 22.

Suitable fastening means are mounted on the pad in the area of overlap for releasably fastening together the overlapped pad ends when mounting the pad collar-wise on the neck of the user. The preferred fastening means comprise burr-type ("Velcro") fasteners 24, 26. Fastener 24 is mounted centrally and longitudinally on the outer surface of the underlapping end of the pad; fastener 26, centrally and longitudinally on the inner surface of the overlapping end of the pad. It is a particular feature of fasteners of this class that they permit longitudinal size adjustment of the pad to fit the neck of the wearer.

Figure 6:
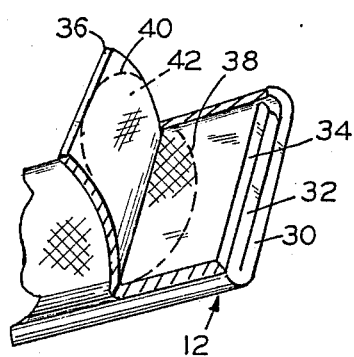
FIG. 6 is a detailed fragmentary view with the parts partly separated, further illustrating the manner of fabricating the collar.
Figure 4:
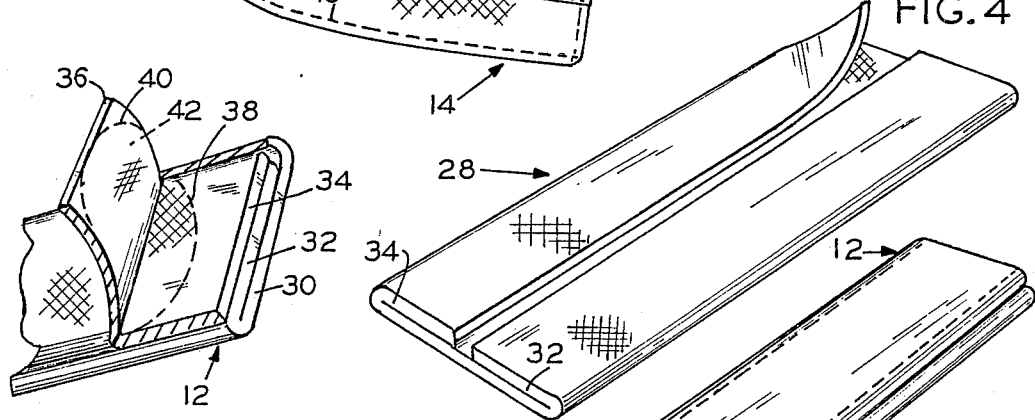
FIGS. 4 and 5 are top perspective views illustrating the manner of folding a piece of thick, absorbent cloth material in the manufacture of the collar.
Figure 5:
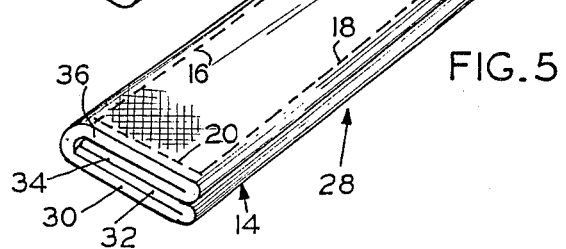

A preferred method of making the herein described collar as illustrated in FIGS. 4, 5 and 6.

As shown in these figures, a rectangular piece of toweling 28 having a length sufficient to encircle the neck and provide an overlap first is processed by folding it longitudinally inwardly from each side to substantially its longitudinal center line, FIG. 4. It then is folded again along its longitudinal center line to form a four ply pad, as shown in FIG. 5. In the illustration, the plies are numbered 30, 32, 34, 36.

The folded plies then may be stitched longitudinally in the manner described above to provide longitudinal stitchings 16, 18, a spaced distance inwardly from the longitudinal margins. This gives body to the pad and maintains it in the desired flat condition. The longitudinal margins thus provided also give support under the chin of the user.

The underlapping end 14 then is secured by transverse stitching 20. Preferably, this is accomplished using a machine which finishes off the raw edges while at the same time creating the row of stitching.

Overlapping end 12, which is visible on the outside of the collar in its use position, preferably is finished off in an attractive manner. This may be accomplished in the manner illustrated in FIGS. 2 and 6.

First, as shown in FIG. 6, the side edges of the plies of the overlapping end are slit and the plies cut off transversely along an arcuate cutting line 38. The ends cut off are discarded.

Top ply 36 however is cut along a matching cutting line 40 a spaced distance outwardly from cutting line 38. The net result is the creation of a tab 42, FIG. 2, which may be folded over the underlying plies and stitched by means of transverse stitch line 22 to create a finished, neat appearing, overlapping end 12.

In the alternative, the end may be processed by means of a machine known in the trade as a "serger", which is provided with an overlock blade and cuts the seam edge, sews the seam, and finishes it off in a single operation.

Figure 1:
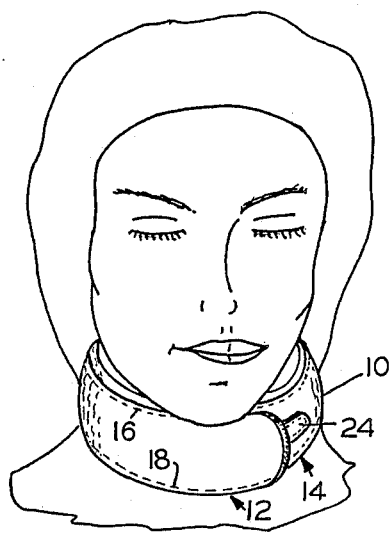
FIG. 1 illustrates the manner of use of the herein described orthopedic cervical support collar.
Figure 3:
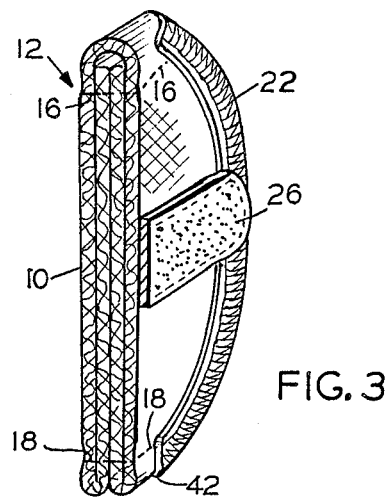
FIG. 3 is a transverse sectional view taken along line 3—3 of FIG. 2.

The finished collar then is applied in the manner shown in FIG. 1. As thus applied, it has many significant advantages:

It fits the size and contour of the neck and gives the desired neck support.

At the same time, it is soft and non abrasive to the skin.

It maintains the head in a superior, natural position.

It allows freedom of natural movement and does not affect the functions of the throat.

It breathes better, is cooler, and does not cause chafing.

It is absorbent and absorbs perspiration efficiently. At the same time, it is susceptible to machine washing and drying so that it may be maintained in a sanitary condition.

A special advantage is that, since it does not put pressure on the neck or head, it allows the wearer to sleep in comfort, while maintaining the neck in correct position.

All of these advantages are obtained, furthermore, by the provision of a collar of simple construction, made inexpensively from a readily obtainable raw material.

Having thus described in detail a preferred embodiment of the present invention, it will be apparent to those skilled in the art that various physical changes could be made in the device described herein without altering the inventive concepts and principles embodied. The present embodiment is therefore to be considered in all respects as illustrative and not restrictive, the scope of the invention being indicated by the appended claims rather than by the foregoing description. All changes which come within the meaning and range of equivalency of the claims are therefore to be embraced therein.

I claim:

1. An orthopedic, cervical, support collar comprising:
   a rectangular piece of thick, absorbent cloth material having longitudinal sides and opposite end portions, folded to form an elongated, multi-plies pad having at least four layers constituting the entire thickness of the collar; said pad having a length sufficient to encircle the neck and provide an area of overlap at said opposite end portions,
   ply interengaging means maintaining the piece in flat, pad-forming condition,
   and releasable fastening means mounted on the pad in the area of the overlap and end portions for releasably fastening together the overlapped end portions when mounting the pad collar-wise on the neck of the user.

2. The collar of claim 1 wherein said rectangular piece is folded longitudinally inwardly from each side to adjacent the longitudinal center line of the piece and then again adjacent the longitudinal center line to form a four-plies pad.

3. The support collar of claim 1 wherein the ply interengaging means comprises stitching through the cloth plies.

4. The support collar of claim 1 wherein the ply interengaging means comprises stitching a spaced distance inwardly along each longitudinal side of the pad to provide stiffened, supportive longitudinal pad margins.

5. The support collar of claim 4, including further stitching transversely adjacent each end portion of the pad.

6. The support collar of claim 1 wherein the fastening means comprises "Velcro" type fasteners.

7. The method of making an orthopedic, cervical support collar which comprises:
   folding a rectangular piece of thick, absorbent, cloth material lengthwise to form an elongated, multiplies pad having at least four layers constituting the entire thickness of the collar and having a length sufficient to encircle the neck and provide an area of overlap at opposite end portions,
   stitching the plies together a spaced distance inwardly of the longitudinal sides of the pad to form stiffened, supportive longitudinal pad margins, and
   mounting on the pad at the overlapped end portions releasable fastener means for releasably fastening together the overlapped end portions when mounting the pad collar-wise on the neck of the user.

8. The method of claim 7 including the steps of folding the piece lengthwise inwardly from each side to adjacent the longitudinal center line of the piece and then against adjacent the longitudinal center line of the piece to form a support pad comprising four plies of substantially uniform size.

* * * * *